United States Patent [19]  [11] 4,332,634
Aperavich  [45] Jun. 1, 1982

[54] METHOD OF PREPARING A RESEALABLE VALVE

[75] Inventor: Steven M. Aperavich, Racine, Wis.

[73] Assignee: Medical Engineering Corporation, Racine, Wis.

[21] Appl. No.: 224,963

[22] Filed: Jan. 14, 1981

[51] Int. Cl.³ .............. A63B 39/00; B29C 17/00; B29C 19/00; A41C 3/10
[52] U.S. Cl. ................................. 156/145; 156/198; 156/213; 156/245; 428/912; 264/257; 264/268; 3/36; 128/349 BV
[58] Field of Search .......... 156/242, 212, 198, 213, 156/218, 224, 145, 146, 229, 115, 245, 307.7; 428/912; 273/65 C; 264/232, 241, 257, 292, 268, 513; 3/36; 137/223, 247.13, 247; 128/214 R, 349 BV

[56] References Cited

U.S. PATENT DOCUMENTS

| 700,656 | 5/1902 | Kemshall | 156/224 |
| 3,600,718 | 8/1971 | Boone | 3/36 |
| 3,799,174 | 3/1974 | Howard | 156/224 |
| 3,919,724 | 11/1975 | Sanders et al. | 128/214 R |

Primary Examiner—Edward C. Kimlin
Assistant Examiner—L. Falasco
Attorney, Agent, or Firm—Quarles & Brady

[57] ABSTRACT

A mehod of preparing a resealable valve which has a resealable inner core and an outer reinforced cover comprises first molding a hollow shell having a domed top and a bottom with a central opening, then turning the shell inside out and affixing a layer containing reinforcing fabric to the inside of the domed top, next turning the shell right side out and covering the bottom including the central opening with a layer containing reinforcing fabric to complete the cover, filling the thus formed cover with an uncured elastomer and finally curing the cover and its elastomer contents to form the resealable valve.

3 Claims, 7 Drawing Figures

METHOD OF PREPARING A RESEALABLE VALVE

The present invention relates to a method of preparing a resealable valve. More particularly, it relates to a method of preparing a resealable valve which can be used to add or remove fluid from an implanted medical device.

BACKGROUND OF THE INVENTION

Resealable valves have been used with medical devices where, for some reason, it is necessry or desirable to add or remove fluid to or from such a device. For example, such valves have been commonly used on inflatable mammary implants in order to inflate the implants to the desired size after they have been implanted through relatively small incisions.

Representative of prior art resealable valves are those shown and described in the Sanders et al U.S. Pat. No. 3,919,724 and the Boone U.S. Pat. No. 3,600,718. Both of the patented valves have shells which are made by hand casting and then filled with a viscous or free-flowing silicone gel.

SUMMARY OF THE PRESENT INVENTION

It is an object of the present invention to disclose a method of preparing a resealable valve with a reinforced cover, and a "hard gel" inner core which has desirable resealing properties.

In the preferred method of the present invention, the valve is prepared by first transfer molding a hollow shell having a domed top and a flat bottom having a central opening. The shell then is turned inside out and a reinforcing fabric affixed to the inside of the domed top. Next, the shell is then turned right side out and the bottom, including the central opening covered with a layer containing a reinforcing fabric. The thus closed shell or cover is then filled with an uncured silicone elastomer "hard gel" mixture and the cover and its silicone gel contents cured to obtain the desired valve.

The method of the present invention provides time and material savings and other advantages which will be apparent to those skilled in the art.

BRIEF DESCRIPTION OF THE DRAWINGS

The invention will be described in connection with the enclosed drawings in which.

DESCRIPTION OF THE PREFERRED EMBODIMENT

Figure 1:
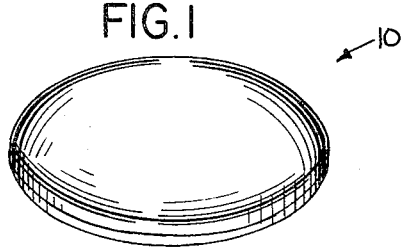
FIG. 1 is a perspective view of a preferred embodiment of the resealable valve of the present invention.
Figure 2:
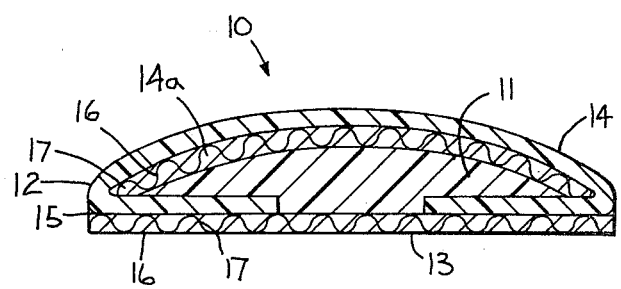
FIG. 2 is a cross-sectional view of the valve of FIG. 1 taken along lines 2—2 of FIG. 1.

As seen in FIGS. 1 and 2 of the drawing, the resealable valve 10 is a generally disc shaped member which has a "hard gel" inner core 11 which is encompassed within a cover 12 of a biocompatible material which is preferably silicone rubber or polyurethane.

Referring specifically to FIG. 2 it can be seen that the cover 12 consists of a flat bottom 13 and a domed shell 14 which are joined together along their respective edges as at 15 to form the completed cover 12. In the embodiment shown, the interior 14a of the top of the domed shell 14 and the exterior of the flat bottom 13 are both covered and reinforced with a layer 16 including a fabric 17 such as dacron.

The inventive method of preparing the valve 10 now will be described in connection with FIGS. 3 to 7.

Figure 3:
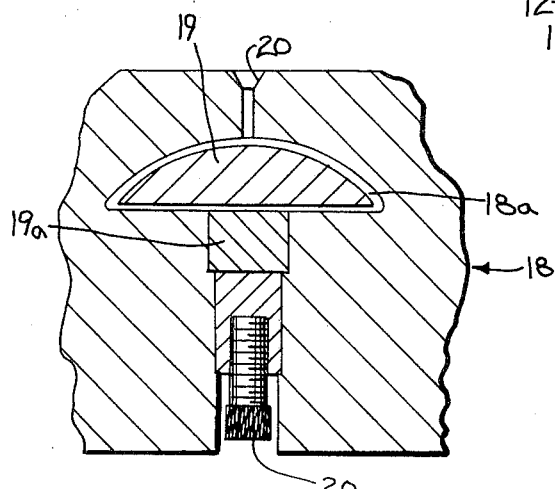
FIG. 3 is a cross-sectional view of a single cavity of a transfer mold used to make the valve shell.

Turning first to FIG. 3, there can be seen a single cavity mold 18 for molding the domed shell 14. Positioned within the cavity 18a is a mushroom shaped insert 19 having a stem 19a. The insert 19 is held in place by a screw 20 which enters the stem 19a. The insert 19 is positioned in the cavity 18 so that an elastomeric material, such as silicone rubber, from which the shell 14 is to be molded can enter the sprue 20 at the top of the cavity 18a and flow completely about the insert 19 to fill the cavity 18a, except for the area occupied by the stem 19a.

Figure 4:
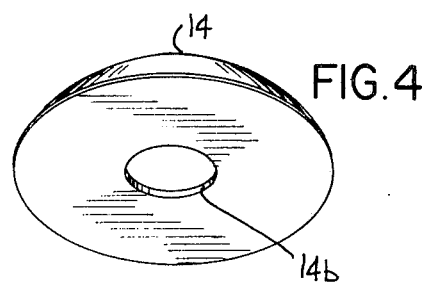
FIG. 4 is a perspective view of a molded valve shell.
Figure 5:
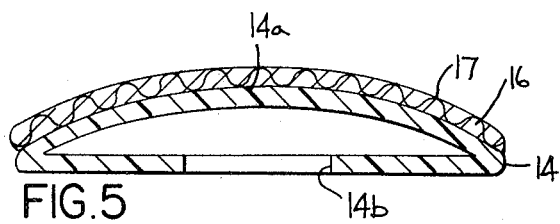
FIG. 5 is a cross-sectional view showing the valve shell of FIG. 4 turned inside out and a reinforcing layer being applied to the inside of the top of the shell.
Figure 6:
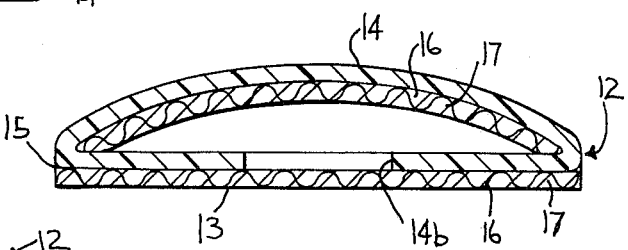
FIG. 6 is a cross-sectional view of the valve shell turned right side out and the bottom being closed with a reinforced sheet.

When the elastomeric material is sufficiently cured as by heating, the mold 18 is opened and the shell 14 stripped from the insert 19 by turning it inside out. The shell 14 as seen best in FIG. 4 is completely closed except for a central opening 14b formed by the stem 19a. As seen in FIG. 5, while the shell 14 is turned inside out, a layer 16 of elastomer containing reinforcing fabric 17 is secured to the interior 14a of the top of the shell 14, preferably with a suitable silicone adhesive. The shell 14 is then turned right side out and the bottom of the shell 14 including the central opening 14b closed with a layer 16 of silicone containing reinforcing fabric 17 (as seen in FIG. 6) to obtain the complete cover 12. The cover 12 is then cured by heating at about 250° F.

Figure 7:
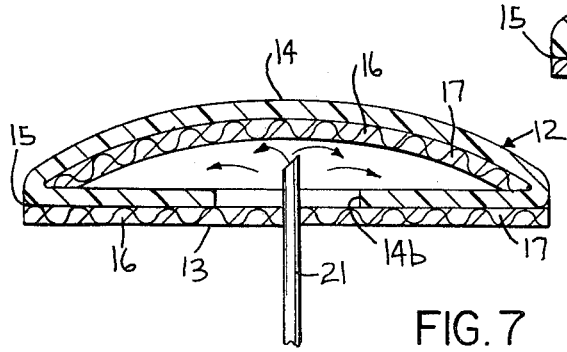
FIG. 7 is a schematic view showing the manner of filling the cover with uncured gel.

As seen in FIG. 7, the cover is filled with the "hard gel" 11 through a cannula 21 which extends through the bottom 13 of the cover 12. When the interior of the cover 12 is completely filled with "hard gel" 11 the cover 12 and its contents are heat cured at about 200° F. for about 3 to 4 hours to produce the finished valve. The preferred valve contains a "hard gel" which upon curing has a penetration reading of about 7.5 mms. to about 12.5 mms. as measured using a penetrometer having a ¼" foot and using a 5 second penetration time.

The preferred "hard gel" is a silicone gel of the type described in U.S. Pat. No. 3,919,724 which after vulcanization is self sealing on penetration by a needle. Self sealing valves made by the method of the present invention may be used in a variety of medical devices such as inflatable mammary prostheses, inflatable penile implants, urinary incontinence controlling devices and the like in which it may be desirable to add or remove fluid from a closed hydraulic system.

While for purposes of illustration a specific detailed method of preparation of a specific resealable valve has been described, it will be appreciated by those skilled in the art that a number of modifications and changes may be made without departing from the spirit of the scope of invention. For example, the method could be used to make valves of all sizes and in place of the transfer molding process described, other molding processes such as injection molding might be used. In addition, other elastomers than those mentioned, including thermoplastic elastomers, and other adhesives may be employed if desired. Therefore, it is to be understood that the scope of the invention is to be limited only by the claims which follow.

I claim:

1. A method of preparing a resealable valve which has a resealable inner core and an outer reinforced cover which comprises first molding a hollow shell having a domed top and a bottom with a central opening, turning the shell inside out, affixing a layer containing reinforcing fabric to the inside of the domed top, turning the shell right side out and covering the bottom including the central opening with a layer containing reinforcing fabric to complete the cover, filling the thus formed cover with an uncured elastomer and then curing the cover and its elastomer contents to form a resealable valve having a resealable hard gel inner core and an outer reinforced protective cover.

2. The method of claim 1 in which the elastomer employed is silicone rubber.

3. The method of claim 1 in which the reinforcing fabric is dacron.

* * * * *